(12) United States Patent
Mehrotra et al.

(10) Patent No.: US 6,860,859 B2
(45) Date of Patent: Mar. 1, 2005

(54) APPARATUS AND METHOD FOR DETECTION OF ESTRUS AND/OR NON-PREGNANCY

(75) Inventors: Vikram P. Mehrotra, Wildwood, MO (US); Chris R. Redford, Webster Groves, MO (US)

(73) Assignee: Monsanto Technology LLC, St. Louis, MO (US)

(*) Notice: Subject to any disclaimer, the term of this patent is extended or adjusted under 35 U.S.C. 154(b) by 195 days.

(21) Appl. No.: 10/124,933

(22) Filed: Apr. 18, 2002

(65) Prior Publication Data

US 2002/0156394 A1 Oct. 24, 2002

Related U.S. Application Data

(60) Provisional application No. 60/285,315, filed on Apr. 20, 2001.

(51) Int. Cl.[7] ............................................. A61B 10/00
(52) U.S. Cl. ........................................ 600/551; 128/903
(58) Field of Search ................................ 600/551, 367, 600/549, 547, 508, 509, 513, 519, 370, 595, 309

(56) References Cited

U.S. PATENT DOCUMENTS

| | | | | |
|---|---|---|---|---|
| 3,297,020 A | | 1/1967 | Mathiesen | |
| 4,224,949 A | * | 9/1980 | Scott et al. | 600/551 |
| 4,515,167 A | * | 5/1985 | Hochman | 600/549 |
| 4,676,254 A | * | 6/1987 | Frohn | 600/549 |
| 4,784,155 A | * | 11/1988 | Mills | 600/547 |
| 5,209,238 A | * | 5/1993 | Sundhar | 600/551 |
| 5,233,984 A | * | 8/1993 | Thompson | 600/595 |
| 5,240,010 A | * | 8/1993 | Weinmann | 600/547 |
| 6,039,923 A | | 3/2000 | Klemm et al. | 422/61 |

* cited by examiner

*Primary Examiner*—Eric F. Winakur
(74) *Attorney, Agent, or Firm*—Grace L. Bonner; Howrey Simon Arnold & White, LLP (57) ABSTRACT

The present invention is directed to devices for detection estrus-state and/or non-pregnancy in mammals and methods for using the same. The device and/or methods may be of particular use in cattle. The devices disclosed include at least a housing of a size, shape, and outer surface quality permitting it to be securely maintained within a mammals vagina. The housing has at least one interior space for installation of instrument(s) for measuring, intra-vaginally, at least on indicia of estrus (heat) or non-pregnancy, converting the resulting measurement into a signal or signals (electronic or otherwise). The device also comprises a signal transmitting means and, optionally, a remote receiving station capable of interpreting the signal(s).

30 Claims, 3 Drawing Sheets

APPARATUS AND METHOD FOR DETECTION OF ESTRUS AND/OR NON-PREGNANCY

This application claims the benefit of U.S. Provisional Application Ser. No. 60/285,315 filed Apr. 20, 2001.

BACKGROUND OF THE INVENTION

Commercial raising of cattle for dairy production requires proper management. In addition to the various husbandry concerns such as herd health and nutrition, a critical management area for economic survival of any cattle operation, is the breeding management of the cows.

Dairy cows are managed intensely and there are costs associated with breeding the cow, how long it takes each cow to become pregnant, as well as associated labor costs. Economics of a dairy make it important to both minimize the amount of time a dairy cow is not pregnant and yet still have a high probability of the cow becoming pregnant.

It is estimated that for every day past a set goal date that a cow remains non-pregnant or open, there is an economic loss of between $1.00-$3.00 per day. An average sized dairy herd is between 200 to 1,000 cows. If the 24 hours during which the cow should be bred is missed for each cow, this represents an economic loss of $4,200.00 to $21,000.00 annually. Often cows are not successfully bred for as many as 3 estrous cycles, due to infertility, infections and semen-related problems. If one half of the cows in a herd of 200 to 1,000 is not impregnated for 3 cycles, the estimated economic loss increases to $6,300.00 to $31,500.00 annually. These projections of economic loss to the producer demonstrate the critical importance of the cow spending the majority of each year producing milk.

Annually 1 million dairy cows are culled for reproductive failure, for reasons such as infertility, and infections.

To improve the management of dairy cows and decrease the economic losses associated with the non-pregnant interval it is desirable to have additional options and management tools other than culling the animals.

There are several variables that can impact the whether or not the cow is successfully bred and becomes pregnant during any particular estrous cycle. The number of times that a cow must be bred before becoming pregnant is traditionally measured as the "service to conception rate." The variables that affect the service to conception rate include semen quality (processing and handling), sperm quantity/quality, breeding technique, and egg quality; all of these variables play major roles.

Still, the most important variable remains in the timing of the insemination. If inseminated too early the sperm may not survive until the optimal 12 hour fertilization window. If inseminated too late the sperm will not reach their destination during the optimal window of time. Finally, if the animal was somehow identified for breeding but is not in estrus, then she will not become pregnant after insemination.

Some dairy producers try to improve this service to conception rate by being extremely conservative (relying on multiple signs of heat) before breeding an animal. While the rate can improve, this means of identification will allow for Type II errors (many cows that are actually in heat will not be bred and thus will miss one more cycle to become pregnant). If a producer decides to liberally breed animals (not on multiple signs) the tendency will be to use lower price semen and thus possibly reduce conception rates and/or decrease the rate of genetic improvement in the herd, group or dairy. Knowing exactly if a cow is in estrus and the best time to breed such animal is very important information to a dairy producer.

There are several easily observable, as well as biological signs that have been identified as indicators of estrus in cattle. Outward signs would include, in order of importance, observed mounting activity, evidence of mounting activity (roughened hair coat increased activity), abnormal social behavior with other animals and the change of appearance of the vulvar region. Biological changes that have been observed could include changes in the following; basal body temperature, mucus conductivity and reproductive hormone levels in blood, tissue and/or milk. The hormones that have the most effect and are most indicative of stage of the estrous cycle are luteinizing hormone, follicle-stimulating hormone, progesterone, estrogen and inhibin.

Currently, the best way to identify animals that should be scheduled for insemination is by identifying the animal in standing heat. This visual method generally requires a half hour observation session twice daily. Even with this concentrated effort, many cows will go unobserved.

Several devices and methods have been used by dairy farmers to aid in this visual observation effort. These methods basically try to mark an animal that has been mounted by another animal. Chin ball markers, dye-release mount detectors, and tail chalking are methods that still require the herd manager to observe the mark on the animal. Recently, there have been some electronic instruments developed to measure mounting activity. There are systems that include a glued-on transmitter that sends identification of mounting activity to a receiver. There are systems that include a glue-on electronic device which counts mounting activity and displays it cow-side. These electronic devices only monitor mounting successes, which by itself still provides for significant type I and type II errors (silent heat—loss of device—accuracy). Of even lesser value are pedometers which simply measure elevated cow activity. These are even less accurate than the mounting sensors.

There is still a need for more accurate and successful estrus detection, particularly in cows.

SUMMARY

The present invention includes an apparatus and methods for using the same. The apparatus is useful for detection of estrus ("heat") or non-pregnancy in a mammal and may be of particularly use in cows, more particularly dairy cows. The device includes at least a housing of a size, shape and outer surface quality permitting its being securely retained within a mammal's vagina. The housing has at least one interior space for installation of instruments for intra-vaginally measuring at least one and preferably at least two physiological conditions of indicative of estrus-state and converting the resulting measurements into electronic signals. The apparatus also has a signal transmitting means and optionally a receiving station capable of interpreting the combination of signals.

DESCRIPTION OF ILLUSTRATIVE EMBODIMENTS

The apparatus and methods of the present invention are useful for the detection of estrus-state in a mammal, and also useful for the detection of non-pregnancy in a mammal (the mammal will not come into heat if pregnant). The invention will be useful in the livestock industries and of particular use in the dairy industry, used in dairy cows.

As used herein the term "estrus-state" refers to the subject mammal's physiological status with regards to the estrus cycle (specifically, whether the animal in estrus ("heat") or not).

In general terms the apparatus of the present invention has a housing of a size, shape and outer surface quality permitting its being securely retained within the mammal's vagina for a period of at least about 48 hours. The housing has at least one interior space suitable for the installation of instruments capable of monitoring and/or measuring at least one and preferably at least two intra-vaginal conditions indicative of estrus-state and converting the resulting measurements into one or more signals (electronic or analog) representing each of said conditions.

The apparatus also has a signal transmitting means for sending said signals to a receiving station located outside of the subject animal (where the receiving station is capable of receiving said signals or optionally capable of receiving and interpreting the said signal(s) to indicate whether the mammal is in estrus), said transmitting means being suitable to be held in continuous proximity to the mammal's body during the time of said measuring, converting and transmitting, of the signal, so that said transmitting means travels with the mammal during said time. In various embodiments of the invention the receiving means does not travel with the subject animal.

In some embodiments of the invention the apparatus comprises a relatively inflexible arm connecting the housing of the apparatus the sending means such that, when the housing is within the mammal's vagina, said sending means is substantially external and proximal with respect to the mammal's body In some embodiments the apparatus includes the housing sized for residence within the mammal's vagina, and having an interior space sufficient in volume to accommodate installation of at least one, and preferably at least two, physiological-parameter sensors. The apparatus also has at least one, and preferably at least two, physiological-parameter sensors, and preferably three or more sensors, disposed within the housing. The apparatus also has a transmitting means functionally associated with the sensors that is capable of transmitting the physiological-parameter signals from the sensor(s). In various embodiments the apparatus can further include a recording device for recording physiological-parameter sensor data. The apparatus may also comprise a remote receiving device for receiving transmissions from the transmitting means.

In various embodiments of the instant invention the apparatus may comprise a means for storing the measured physiological-parameter sensor data and transmitting the data intermittently (i.e., once per time period, for example, once every 20 minutes), or transmitting the data in response to an electronic query. The apparatus may also comprise a means of actively transmitting the measured data. Alternatively, the device may be capable of continuous data transmission. The term "continuous data transmission" may mean that the transmitter is sending an uninterrupted signal. Alternatively, "continuous data transmission" may mean that the data is transmitted as it is measured (e.g. once per second, once per minute, once per ten minutes, and etc.).

In various embodiments the transmitting means, for the apparatus, may also comprise a transmitter and an antenna.

In particular embodiments the antenna may comprise a substantially co-axial extension operably connected with the apparatus. The extension being of such dimension and position on the apparatus so as to provide for a portion which is exterior to the mammal when the apparatus is inserted into the mammals vagina. In an even more particular aspect of this embodiment the antenna further comprises a second extension which is fixedly and orthogonally attached to the co-axial extension.

In any embodiment it is most desirable that the physiological parameters or intravaginal conditions, to be measured or sensed, be selected from the list consisting of: heart rate; body temperature; viscosity, pH, and/or conductivity of the vaginal mucous or tissue; animal movement or motion; and/or reproductive hormone levels. The hormones that have the most effect and are most indicative of stage of the estrous cycle are luteinizing hormone, follicle-stimulating hormone, progesterone, estrogen and inhibin. This list is not meant to be exhaustive, but only illustrative, to one skilled in the art, of physiological parameters or intravaginal conditions which can be measured or sensed.

Preferably the parameters to be measured are selected from the listing consisting of heart rate; body temperature; viscosity, pH, and/or conductivity of the vaginal mucous or tissue; and movement or motion of the monitored animal. More preferably the measured conditions are selected from the group consisting of animal movement or motion, animal body temperature, and vaginal fluid conductivity and/or viscosity.

In any embodiment the apparatus may optionally and desirably include a power source such as a long-life battery, solar cell or battery, methane-powered battery, rechargeable battery or other suitable power source.

In any embodiment the transmission of the signals may be passive or active or on demand, such as when queried by another electronic device. Examples of transmitting and/or receiving devices include mobile devices such as a handheld phones or PDAs (personal digital assistants); or stationary devices mounted on a fence, pole, in the milking parlor the animal visits, or other appropriate location.

In any embodiment the housing may be manufactured separately from the measuring or sensing devices or it may alternatively be manufactured as an integral unit. Methods and materials for manufacturing devices to be biocompatible within a mammals body are well known to those skilled in the art. Examples of material that are suitable are non-reactive plastics, surgical-use metals and composite materials having biocompatible properties.

In preferred embodiments, the housing and any extension or antenna has an essentially smooth outside surface. Those skilled in the art will appreciate that the housing may also have an outside surface that is dimpled, ridged, spongy or otherwise having texture or relief thereon and still be within the scope of the invention as claimed herein. Likewise, in preferred embodiments the housing is substantially cylindrical it may also be frustoconical, spiral or helical, substantially rectangular with rounded sides or similarly dimensioned polygonal shape.

Figure 1:
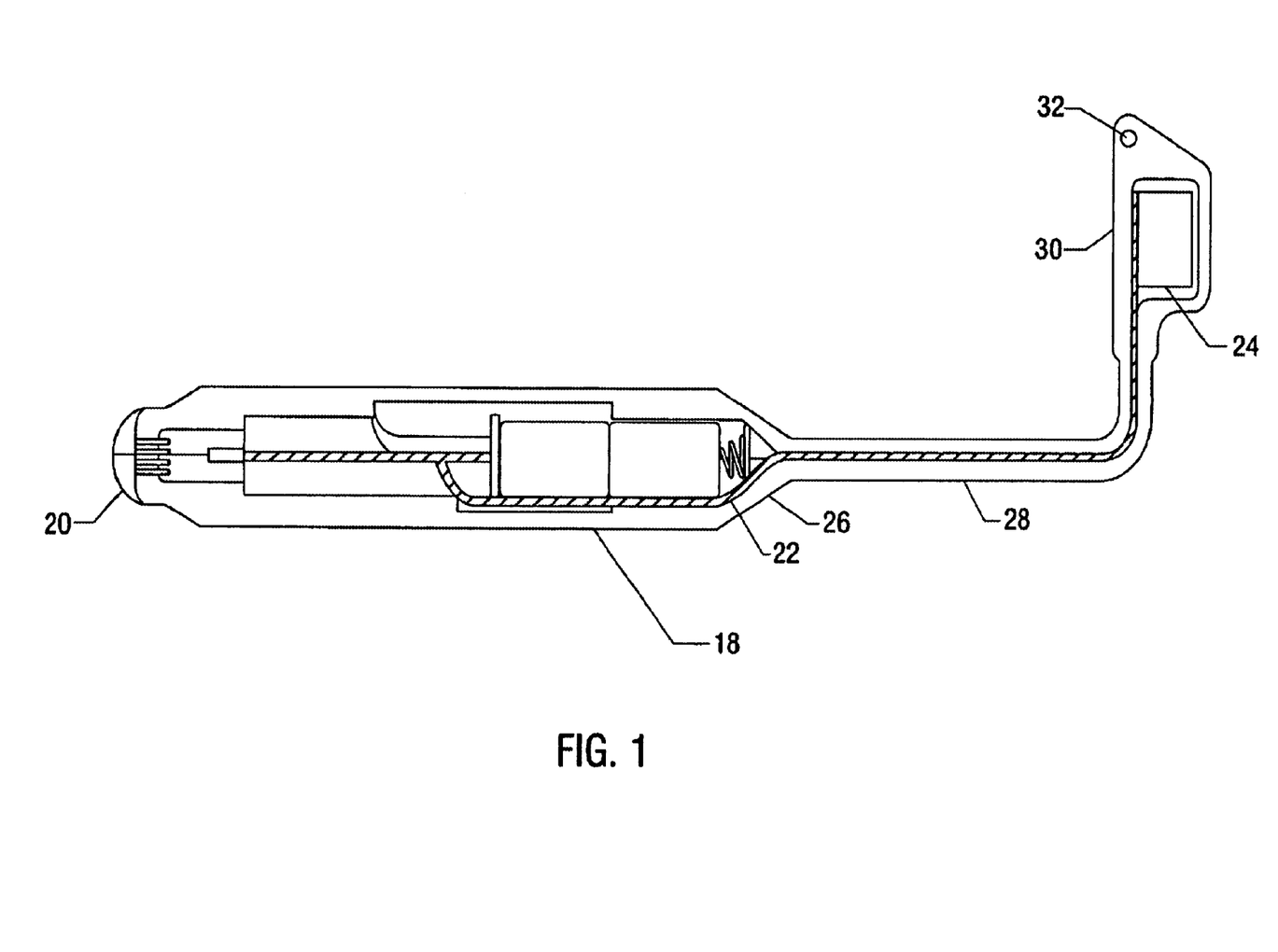
FIG. 1. is a schematic of a preferred embodiment of the invention
Figure 2:
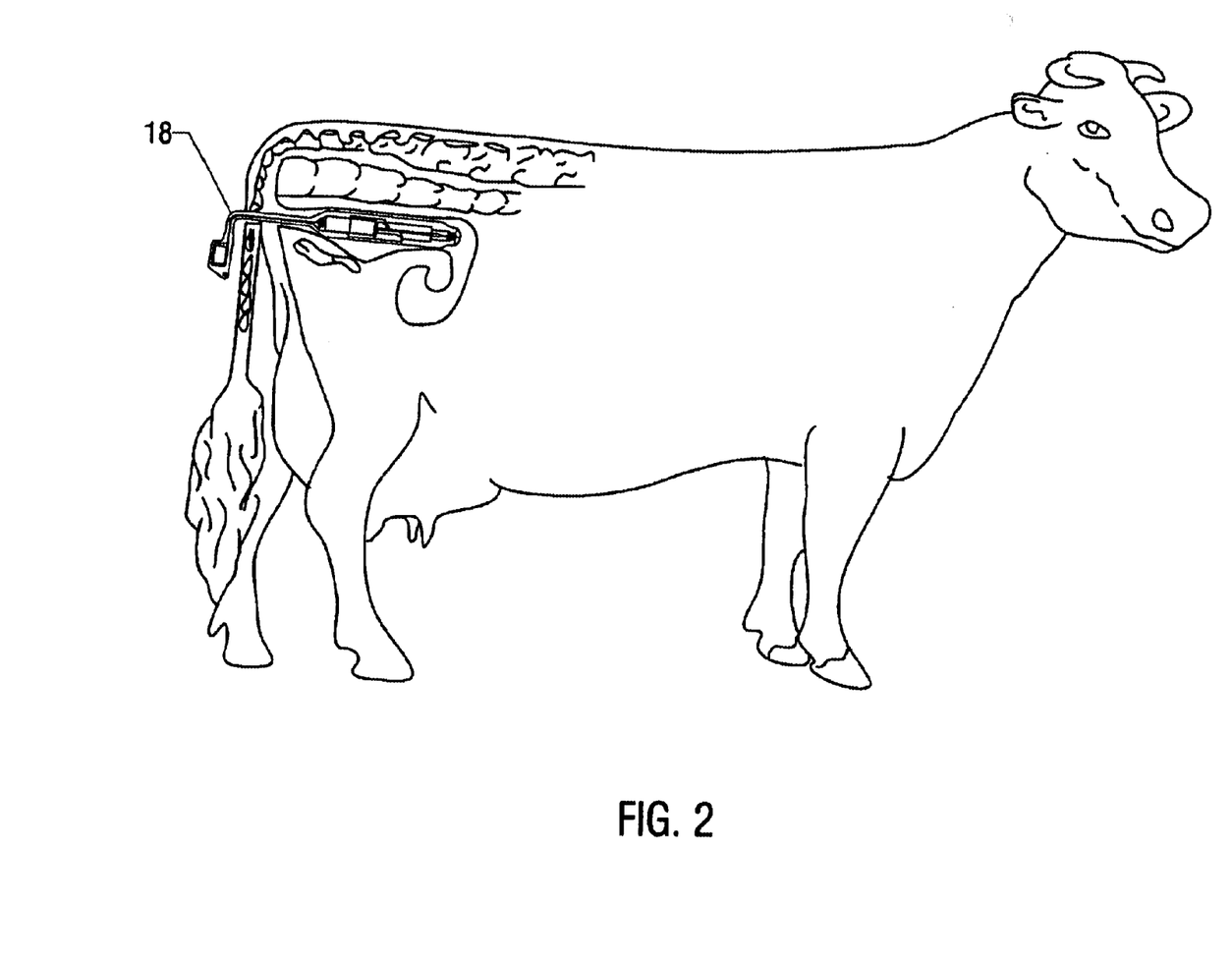
FIG. 2 is a environmental view of the apparatus in use

In one preferred embodiment the apparatus is sized and shaped in approximate accordance with the device illustrated in FIG. 1. Those skilled in the art will recognize that the invention will work as well in embodiments having other physical configurations than the two extensions that are longitudinal and orthogonal to the housing.

The apparatus may be used in accordance with any of the methods disclosed or suggested herein Briefly, the method of the present invention comprises using any of the embodiments of the above described device to sense, within the vagina of the mammal, at least one, and preferably at least two, condition(s) indicative of estrus-state, and more preferably three or more conditions or parameters. Preferably such sensing for the plurality of conditions or events is conducted essentially concurrently or simultaneously, but in some embodiments the sensing may be alternating sensing and/or at alternating intervals. The sensed condition, data or information is transmitted as signals (electronic or otherwise) representing each of said conditions from a location proximal and exterior to the mammal's body. The transmissions or recorded data of the combination of signals is then interpreted to provide an assessment of whether the mammal is in estrus, according to predetermined criteria and/or reference data. By way of non-limiting example, a cow's temperature and conductivity (of either the vaginal fluid, mucosa or local tissue) may be measured or the rate of change in those parameters may be measured and then those data may be compared to data or events historical to the individual animal or like animals that are known to be in estrus (this may also be referred to as reference data) and if the measured or recorded conditions or events are acceptably close to the reference data information the cow or other mammal would be considered to be in estrus.

It is envisioned that the referenced data may be based on either data collected from the same animal in a prior estrus cycle or it may be based on data collected by monitoring a plurality of animals during their respective estrous cycles and plotting ranges and/or threshold limits for the values deemed to indicate that the animal is in heat.

Similarly if the animal has been bred and the apparatus and method demonstrate that the animal is in estrus the animal is considered to be non-pregnant.

The apparatus is inserted into a cow's vagina and may be most preferably secured there using a retention device as described below.

Figure 3:
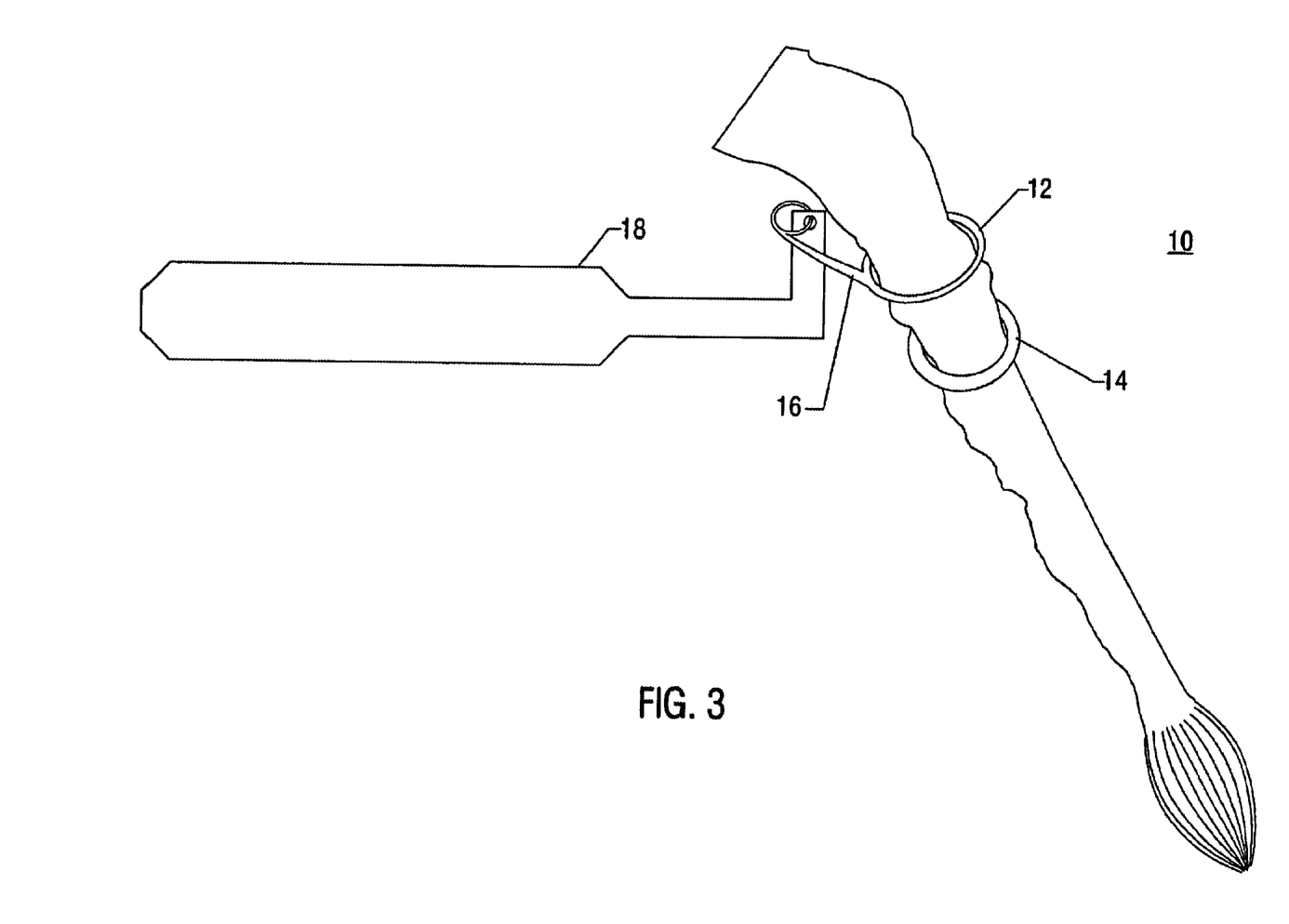
FIG. 3 is a schematic of a preferred retention device for use with the instant invention.

In use, the apparatus of the present invention is most desirably retained in the cow's vagina with an intravaginal retention device 10 (designed to successfully retain estrus-state detection device in the cow's vagina for a period of over 14 days or more). The device 10 is comprised of a first tail anchor or ring 12, a second tail anchor or ring 14 both of which substantially surround the tail of the animal, a tether 16 of specified length and optionally, main body or housing 18. Although it is not necessary for anchors 12 and 14 to be annular in shape or completely encircle the animal's tail, for purposes of example anchors 12 and 14 are described herein as "rings." The length of tether 16 allows the device 10 to move slightly but prevents housing 18 from being expelled from the animal's vagina. The first tail ring 12 is prevented from slipping down the tail (which then would lead to expulsion of the housing 18) by a second tail ring 14 on the tail, most preferably located caudally (i.e., towards the end of the tail rather than body) and in close proximity to first tail ring 12. The position of second tail ring 14 on the tail is preferably about 5 cm down from the tail head, but in any event second tail ring 14 is anatomically positioned so that movement of first tail ring 12 on the cow's, or other animal's tail will not cause sufficient tension on tether 16 to dislodge housing 18 from the cow's vagina.

In some embodiments first ring 12 and second 14 may be in spaced apart, fixed connection with each other, such as by means of one or more connectors 15. In other embodiments first ring 12 and second ring 14 are not connected to each other but are spaced apart positionally from each other to prevent tether 16 from becoming so taut as to cause housing 18 to be dislodged from the cow's vagina.

The optional main body 18 of device 10 can be made hollow to accommodate sensors and electronics to use it as sensing device to measure various parameters that indicate an animal's status. It can also be used as a vaginal drug delivery device by attaching drug delivery device or other components with the retention device 10.

Tether 16 may be fixedly or removably attached to optional main body 18. Likewise, tether 16 may be fixedly or removably attached to first tail anchor or ring 12. Means by which tether 16 may be attached to either main body 18 and/or first tail ring 12 include, but are not limited to integral manufacture with main body 18, swivel-ring or other rotating means attachment, VELCRO™, any detent mechanism, any type of clasp or clip, permanent attachment by glue, screws, rivets, welding or other appropriate means of attachment. The tether 16 is most preferably composed of any non-stretchable plastic, metal, silk or any other appropriate material, however materials that have stretch or elastic characteristics may also be used.

The main body 18 of the device 10 can be made out of any biocompatible material, such as plastics, metals, and elastomeric or spongy materials or any suitable composite materials. Both first tail ring 12 and second tail ring 14 may be composed of be plastics, metals, elastomeric or spongy materials or combinations thereof. It is not necessary for the first ring 12 and second ring 14 to be made of the same material. For example first ring 12 may be manufactured of metal or plastic and second ring 14 may be composed of a spongy material or a series of circumferences of elastomeric tape around the animal's tail.

In any embodiment of the invention, first ring 12 and second ring 14 must be sized appropriately in relation to the animal on which device 10 is going to be used. Ring 12 and 14 must surround the tail in such a fashion as to not constrict the blood flow in the tail of the animal to an extent that such constriction causes tissue necrosis. Second ring 14 must be in sufficient fixed contact with the tail to prevent the caudal movement of first ring 12 past second ring 14. First ring 12 may fit and surround the tail in such a fashion as to remain relatively fixed in position or may be sized to move somewhat freely above second ring 14.

EXAMPLES

The estrus-state detection device of the instant invention functions based on the fact that at the time of estrus (heat) there are physiological and chemical changes that take place in and/or can be monitored from the vagina of a mammal which indicate that the mammal is in estrus or heat. The present invention is directed to devices and methods for continuously monitoring for and/or detecting the occurrence of such changes and then reporting the onset of estrus when one or more of the monitored parameters indicate the onset of estrus.

For example, at the time of estrus, the conductivity of the vaginal fluid increases, the temperature goes down just before estrus and then rises again, the pH and the viscosity of the vaginal fluid changes, a graph of the measured concentration of certain hormones e.g., progesterone, luteinizing hormone, etc. show characteristics peaks and valleys, the animal's heart rate increases, and animals become more agitated and therefore exhibit more movement and/or restlessness.

Various embodiments of the instantly disclosed device comprise several sensors to monitor selected parameters of interest, an electronic means of storing the information collected by the sensors and finally an electronic, or other type, means of transmitting the stored information to a receiving station. The receiving station then can be hardwired or wirelessly linked to a computer to display information and based on selected algorithms indicate the estrus-state of any monitored animals, including which, if any of the animals are in heat.

In one embodiment of the instant device comprises at least three sensors: a temperature sensor, a conductivity sensor and a motion sensor (all three of which are housed inside the device). The device can then be inserted in the cow's vagina and held in place via a retention mechanism.

In one aspect of this embodiment the device also houses a printed circuit board that has electronic components to collect the sensor input, store the information, and/or to transmit the information to the receiver station at a programmed and predetermined time interval. The device also comprises a battery to provide energy to power the electric components, which may include an electronic circuit and for transmitting the information.

An antenna system may is incorporated into various embodiments of the instantly disclosed device and is preferably chosen so as to be capable of efficiently transmitting the measured information a distance of at least about 30 to 50 ft, although a transmission system with a shorter range is also envisioned.

Temperature sensors used as part of the instant device and/or methods may be any which are suitable for use according to the instant invention. Suitable temperature monitoring sensors, include those having a precision and/or accuracy of about 0.05 to 0.1° C., are commercially available. The typical range of temperature measurement is from about 37° C. to about 43° C., although there may be some variance from this range.

While it may, the temperature sensor need not have direct contact with the subject animal. It may, instead, be mounted on a printed circuit board inside of the device. In this configuration, the sensor is not in direct contact with the vaginal fluid. Nevertheless, a change in the temperature in the vagina produces a corresponding change in the interior temperature of the device, which is detected by the temperature sensor. It is this type of change in temperature that the sensor may monitor in a continuous manner.

An electronic clock or a microprocessor (preferably as part of the electronic circuitry on the printed circuit board) may be employed to control the timing and frequency of data collection. The data collection and transmission frequency may also be altered and controlled by the microprocessor. In a preferred embodiment, temperature data is collected every 20 minutes and stored in the memory chip. This information is, in turn, transmitted to a receiver every 12 hours.

When employed in various aspects of the current device, conductivity is typically monitored by measuring the current flow between two or more, electrodes mounted on or in functional electrical contact with the external surface of the disclosed device. The amount of current flow between the electrodes is a direct function of the conductivity of the vaginal fluid between the electrodes. Current flow may be measured, either directly or indirectly, using any suitable means including, but not limited to, an ammeter or an ohmmeter.

Electronic leads from the surface mounted electrodes are brought inside the retention device for connection to the electronics and the energy source. Holes though which the lead wires pass into are carefully sealed to protect the electronics inside. Just as in the case of temperature monitoring, the frequency of data collection from the conductivity sensor is also controlled by the microprocessor. Electrodes for use according to the instant invention are preferably constructed to be capable of measuring conductivity in the range of about 1 millimhos/cm to about 100 millimhos/cm with an accuracy and or precision of about 0.2-0.5 millmhos/cm. Electrodes and leads are preferably constructed from material that will not corrode in the vagina or be toxic to the animal. Preferably examples include, but are not limited to, gold, platinum coated wire or stainless steel wire.

The state of restlessness that accompanies estrus condition may be sensed by using a motion sensor of any type suitable for use according to the present invention. For example the motion sensor may be an accelerometer based sensor or a simple on-off switch-type device. According to this embodiment of the invention, every time the animal moves, the accelerometer or the switch generates an electronic signal that is used as an input to an electronic counter in the circuitry. The electronic counter keeps a tally of the number of counts per pre-established time interval. In a preferred aspect of this embodiment of the invention, the counter keeps a tally of the counts per each 20-minute interval. As with temperature and conductivity data, the motion sensor data may also transmitted to the receiver station every 12 hours or as directed by the microprocessor.

Any other number of desired sensors may also be added to the device (e.g., a pH sensor or a heart rate monitor could also be included). The desired complexity of the system, cost of the device, and empirically determined usefulness of the information for a given animal may be used to dictate what parameters should be measured.

In a particular embodiment of the instant invention, the electronic components of the device comprises the following components: (i) a microprocessor (which may be employed to receive sensor inputs, to store data, to control frequency of data collection and/or to direct transmission); (ii) a transmitter or a transceiver (preferably, but not necessarily, in megahertz to gigahertz range); (iii) an antenna; and (iv) a switch mechanism to turn the device on/off and/or to reset it. All these components are preferably housed in the device to be is inserted in the vagina. In addition, a receiver (which could also be a transceiver) with an antenna may be employed to receive the information that the device's transmitter transmits. The receiver system is preferably external to the device and may be generally located such that the cows with devices are within about 30 to 50 feet distance (however, technology which allows this distance to be significantly greater, may also be employed). Data from the receiver may be manipulated and displayed on a computer that may be either hardwired, wirelessly linked, or linked by modem, or other internet connection to the receiver.

In a practical application of the device, cows to be monitored are fitted with the device (which transmits a unique identification code) and the device is turned on. Temperature, conductivity and motion sensor data are collected through out the day as per programmed instructions and stored in the device. The receiver station (along with its antenna) is conveniently located in the milk parlor. When cows enter the parlor, a triggering mechanism triggers the transmission of stored data (along with the device identification code) to the receiver. Alternatively, receiver can send a query to the transmitter in the device and then receive data on demand. Data from the receiver may then be displayed on the computer screen along with the cow identification. Data can be displayed in a tabular form or in a graph form. Alerts and alarms can be programmed in the software to trigger when the data collected falls within a range (which may be determined empirically, for a given cow or may be based on tabulated data) which indicates that a cow is in estrus. A daily summary report can then be created and printed to notify the dairy herd manager which of his/her cows are in estrus.

A fixed receiver station is not the only way of receiving data from device transmitter. In a different embodiment of the system, a handheld device such as a PALM™ pilot or other PDA (personal digital assistant) can be used as a receiver. Technology is commercially available such that the handheld devices can be used to query the estrus-state detection device and receive and analyze the data. Alternatively, the data stored in the PDA can subsequently be directly downloaded into or otherwise transmitted a computer for further analysis.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

We claim:

1. An apparatus, useful for monitoring the estrus-state and/or non-pregnancy of a tailed mammal, comprising:
    (a) a housing, suitable for being maintained within the vagina of said tailed mammal for at least about 48 hours and having interior space suitable for installation of one or more means for monitoring, intra-vaginally, at least one physiological parameter(s) indicative of said estrus-state;
    (b) monitoring means, suitable for being disposed within said interior space, for:
        (i) measuring each of said parameters, and
        (ii) converting the resulting measurements into one or more signals representing each of said parameters;
    (c) means for transmitting said signal(s) to a receiving station located outside the mammal and capable of receiving and interpreting said signal(s) to indicate whether the mammal is in estrus, and
    (d) a relatively inflexible arm connecting said housing with said transmitting means such that, when the housing is within the mammal's vagina, said transmitting means is capable of being substantially external and proximal to the mammal's body.

2. The apparatus of claim 1, further comprising a recording device capable of recording said signal(s).

3. The apparatus of claim 1 or 2 comprising means for intra-vaginally monitoring two or more physiological parameters indicative of estrus-state.

4. The apparatus of claim 1 or 2, said parameters selected from the group consisting of: pH, temperature, conductivity, heart rate, viscosity, motion, luteinizing hormone level, follicle-stimulating hormone level, progesterone level, estrogen level and inhibin level.

5. The apparatus of claim 1 or 2, capable of transmitting said signal(s) continuously.

6. The apparatus of claim 1 or 2, wherein said transmitting means is capable of intermittent transmission of said signal(s).

7. The apparatus of claim 1 or 2, wherein said transmitting means is capable of transmitting said signal(s) in response to an electronic inquiry.

8. The apparatus of claim 1 or 2, wherein the transmitting means comprises an active transmitter.

9. The apparatus of claim 1 or 2, capable of being used to monitor the estrus-state of a bovine.

10. The apparatus of claim 1 or 2, wherein the transmitting means is capable of being held in continuous proximity to the mammal's body, such that said transmitting means is capable of traveling with the mammal during said period of at least about 48 hours.

11. The apparatus of claim 1 or 2 further comprising a receiving device for receiving transmissions from the transmitting means.

12. The apparatus of claim 1 or 2 wherein said measured parameters are selected from the group consisting of temperature, conductivity, and motion.

13. The apparatus of claim 1 or 2 wherein the measured parameters comprise temperature, conductivity, and motion.

14. The apparatus of claim 1 or 2 wherein the transmitting means comprises a transmitter and an antenna.

15. The apparatus of claim 14 wherein the antenna comprises substantially co-axial extension operably connected to the apparatus, said extension being of a dimersion and position on the apparatus that the extension has a portion which is exterior to the mammal.

16. The apparatus of claim 15 further comprising a second extension fixedly and orthogonally attached to the co-axial extension.

17. The apparatus of claim 1 or 2 wherein the receiving station does not travel with said mammal.

18. A method, for detecting estrus-state and/or non-pregnancy in a tailed mammal, comprising:
    (a) monitoring, from within the vagina of the mammal, one or more parameter(s) which are indicative of estrus-state using an apparatus according to claim 1;
    (b) transmitting signals representing each of said parameters from a location substantially adjacent the mammal's body; and
    (c) interpreting the combination of said signals to provide an indication of whether the mammal is in estrus.

19. The method of claim 18 wherein the monitoring of the parameters occurs substantially concurrently.

20. The method of claim 18, said parameters selected from the group consisting of: pH, temperature, conductivity, heart rate, viscosity, motion, luteinizing hormone level, follicle-stimulating hormone level, progesterone level, estrogen level and inhibin level.

21. The method of claim 18 wherein the monitored parameters are selected from temperature, conductivity, and motion.

22. The method of claim 21 wherein temperature, conductivity, and motion comprise the monitored parameters.

23. The method of claim 18 wherein said signals are transmitted continuously.

24. The method of claim 18 further comprising receiving said signals using a receiving means capable of receiving and interpreting the signals to determine whether the mammal is in estrus.

25. The method of claim 18 comprising measuring two or more physiological parameters which are indicative of estrus-state.

26. The apparatus of claim 1 further comprising a means for attaching a tether capable of being secured to the animal's tail.

27. The apparatus of claim 1 which is capable of being retained in the tailed mammal's vagina for periods of over 14 days.

28. A method for determining the optimal time for breeding a tailed mammal to achieve pregnancy, the method comprising:

(a) disposing within a tailed mammal's vagina an apparatus comprising:
 i. a housing sized for residence within the mammal's vagina, and having a space to accommodate installation of one or more physiological-parameter sensors;
 ii. one or more physiological-parameter sensors, disposed within said housing, each capable of measuring said parameter(s) and converting said measurement(s) into one or more signals representing each of said parameters;
 iii. a transmitting means for transmitting said signal(s) to a receiving station capable of receiving and interpreting said signal(s) and
 iv a relatively inflexible arm connecting said housing with said transmitting means such that, when the housing is within the mammal's vagina, said transmitting means is capable of being substantially external and proximal to the mammal's body;

(b) measuring one or more physiological parameters and transmitting one or more signals representing said measurements to a receiving station;

(c) interpreting the transmitted signal(s) to provide measured data regarding the physiological parameter;

(d) comparing said measured data to a set of reference data; and (e) selecting a time to breed the mammal, based on the data comparison.

29. The method of claim 28 wherein the time to breed is selected when the measured data is acceptably close to the reference data, based on predetermined set of conditions.

30. The method of claim 28 which comprises measuring two or more physiological parameters.

* * * * *

UNITED STATES PATENT AND TRADEMARK OFFICE
CERTIFICATE OF CORRECTION

PATENT NO. : 6,860,859 B2
DATED : March 1, 2005
INVENTOR(S) : Vikram P. Mehrotra and Chris R. Redford It is certified that error appears in the above-identified patent and that said Letters Patent is hereby corrected as shown below:

<u>Column 10,</u>
Line 22, delete "dimersion" and insert -- dimension -- therefor.

Signed and Sealed this

Seventeenth Day of May, 2005

JON W. DUDAS
*Director of the United States Patent and Trademark Office*